United States Patent
Lin et al.

(10) Patent No.: US 9,017,611 B2
(45) Date of Patent: Apr. 28, 2015

(54) BIOCHIP

(75) Inventors: Pai-Yang Lin, New Taipei (TW);
Yih-Far Chen, New Taipei (TW);
Chin-Kuan Lin, New Taipei (TW);
Hsiang-Chia Chen, New Taipei (TW);
Sheng-Hsiung Weng, New Taipei (TW)

(73) Assignee: Wistron Corporation, New Taipei (TW)

( * ) Notice: Subject to any disclaimer, the term of this patent is extended or adjusted under 35 U.S.C. 154(b) by 114 days.

(21) Appl. No.: 13/430,715

(22) Filed: Mar. 27, 2012

(65) Prior Publication Data

US 2013/0104632 A1 May 2, 2013

(30) Foreign Application Priority Data

Nov. 2, 2011 (TW) .............................. 100140034 A

(51) Int. Cl.
*G01N 33/00* (2006.01)
*B01L 3/00* (2006.01)
*G01N 1/00* (2006.01)
*G01N 15/14* (2006.01)
*G01N 15/10* (2006.01)

(52) U.S. Cl.
CPC .... *G01N 15/1459* (2013.01); *G01N 2015/1006* (2013.01); *G01N 15/1404* (2013.01); *G01N 15/1484* (2013.01)

(58) Field of Classification Search
CPC .......... G01N 15/1404; G01N 15/1484; G01N 2015/1006
USPC .................................................... 422/73, 502
See application file for complete search history.

(56) References Cited

U.S. PATENT DOCUMENTS

| | | | |
|---|---|---|---|
| 2002/0025280 A1* | 2/2002 | Chazan et al. | 422/102 |
| 2005/0011764 A1* | 1/2005 | Berndt et al. | 204/600 |
| 2010/0310421 A1* | 12/2010 | Oliver et al. | 422/82.01 |
| 2011/0014096 A1* | 1/2011 | Fukuoka et al. | 422/503 |
| 2011/0020876 A1* | 1/2011 | Wilding et al. | 435/91.2 |
| 2011/0118139 A1* | 5/2011 | Mehta et al. | 506/9 |

FOREIGN PATENT DOCUMENTS

WO 0078454 12/2000

OTHER PUBLICATIONS

"Office Action of China Counterpart Application", issued on Jun. 5, 2014, p. 1-p. 14, with a partial English translation thereof.

(Continued)

*Primary Examiner* — Jill Warden
*Assistant Examiner* — Brittany Fisher
(74) *Attorney, Agent, or Firm* — Jianq Chyun IP Office

(57) ABSTRACT

A biochip including a chip body, a first electrode and a second electrode is provided. The body has a first accommodating cavity, a second accommodating cavity and a micro-fluid channel. The micro-fluid channel is connected with the first accommodating cavity and the second accommodating cavity. The first electrode has a first end and a second end. The first end is used for contacting a first probe of a detection apparatus. The second end is positioned in the first accommodating cavity. The second electrode has a third end and a forth end. The third end is used for contacting a second probe of the detection apparatus. The forth end is positioned in the second accommodating cavity.

8 Claims, 4 Drawing Sheets

(56) References Cited

OTHER PUBLICATIONS

"Office Action of Taiwan Counterpart Application", issued on Apr. 10, 2014, p. 1-p. 9.

"Office Action of Taiwan Counterpart Application", issued on Oct. 16, 2014, with English translation thereof, p. 1-p. 9.

* cited by examiner

BIOCHIP

CROSS-REFERENCE TO RELATED APPLICATION

This application claims the priority benefit of Taiwan application serial no. 100140034, filed on Nov. 2, 2011. The entirety of the above-mentioned patent application is hereby incorporated by reference herein and made a part of this specification.

TECHNICAL FIELD

The invention relates to a chip, more particularly to a biochip.

BACKGROUND

Currently, a large selection of biochip detection apparatuses is provided in the industry, and a flow cytometer is one type of biochip detection apparatus. Flow cytometry is technique used for identifying and separating cells suspended in a stream of fluid. This technique is also applicable to detect physical properties of cells.

When a flow cytometer is used for cell separation and identification, a charge is selectively applied to the cells. After passing through an electric field, these cells deviate from the original path and flow out from a different exit. Accordingly, the cells can be accurately and rapidly separated from a cell mixture.

When a flow cytometer, which includes a plurality of light sources and optical detectors, is used for detecting the physical properties of cells, as cells suspended in the stream of fluid pass through a light beam, light is scattered. Further, the cells may be excited into emitting a fluorescent light at a frequency lower than that of the light source.

FIG. 1 is a schematic diagram of a conventional biochip. Referring to FIG. 1, after placing a fluid containing the to-be-detected cells inside the biochip, the user places a probe, serving as an electrode, to directly contact the fluid on the biochip 10 and to apply a bias to cause the fluid containing to-be-detected cells to flow in the micro-fluid channel. The flow cytometer then emits a detection light beam, causing each cell suspended in the fluid passing through the detection light beam to generate a fluorescent reaction. The changes of the scattered light and the fluorescent reaction are recorded by the light detector 20. According to the detection result of the light detector 20, the physical and the chemical properties of the cells are calculated. However, prior to performing the next detection, the probe 30 used to directly contact the fluid containing the to-be-detected cells must be thoroughly cleaned to avoid contaminating the next samples.

SUMMARY

An exemplary embodiment of the invention provides a biochip, wherein the problem of contamination generated due to a direct contact of the probe with the fluid containing the to-be-detected cells is resolved.

An exemplary embodiment of the invention provides a biochip that includes a chip body, a first electrode, and a second electrode. The chip body includes a first accommodating cavity, a second accommodating cavity, and a micro-fluid channel. The micro-fluid channel is connected with the first accommodating cavity and the second accommodating cavity. The first electrode and the second electrode are disposed at the chip body. The first electrode includes a first end and a second end, wherein the first end serves to contact the first probe of a detection apparatus, while the second end is configured in the first accommodating cavity. The second electrode includes a third end and a fourth end, wherein the third end serves to contact with a second probe of the detection apparatus, while the fourth end is configured in the second accommodating cavity.

According to an exemplary embodiment of the invention, the above chip body includes a first substrate and a second substrate. The first electrode and the second electrode are disposed on the substrate. The second electrode includes a first through hole, a second through hole, and the micro-fluid channel. The second substrate is disposed on the first substrate, not covering the first end and the third end. The first through hole and the second through hole respectively expose the second end and the fourth end. The first through hole forms a first accommodating cavity, while the second through hole forms a second accommodating cavity.

According to exemplary embodiment of the invention, the above chip body includes a first substrate and a second substrate. The first substrate includes a first through hole and a second through hole. The first electrode and the second electrode are disposed on the first substrate. The second end surrounds the first through hole, and the fourth end surrounds the second through hole. The second substrate includes a first cavity, a second cavity, and the micro-fluid channel. The second substrate is disposed on the first substrate, not covering the first end and the third end. The second end and the fourth end are respectively exposed at the first cavity and the second cavity. The first through hole and the first cavity form the first accommodating cavity, while the second through hole and the second cavity form the second accommodating cavity.

According to exemplary embodiment of the invention, the above chip body includes a first substrate, a second substrate, and a third substrate. The first substrate includes a first cavity, a second cavity, and a micro-fluid channel. The second substrate includes a first through hole and a second through hole, wherein the second substrate is disposed on the first substrate. The first electrode and the second electrode are disposed on the second substrate. The second end surrounds the first through hole, and the fourth end surrounds the second through hole. The third substrate includes a third through hole and a fourth through hole, wherein the third substrate is disposed on the second substrate, not covering the first end and the third end. The third through hole and the fourth through hole respectively expose the second end and the fourth end. The first cavity, the first through hole, and the third through hole form the first accommodating cavity, while the second cavity, the second through hole, and the fourth through hole form the second accommodating cavity.

According to exemplary embodiment of the invention, the biochip further includes a shielding layer. The shielding layer includes an optical window corresponding to a section of the micro-fluid channel.

According to exemplary embodiment of the invention, the first electrode, the second electrode, and the shielding layer belong to a same patterned metal layer.

According to exemplary embodiment of the invention, the biochip further includes a third electrode. The third electrode is disposed at the chip body. The third electrode includes a fifth end and a sixth end. The chip body further includes a third accommodating cavity connected to the micro-fluid channel, and the fifth end serves to contact a third probe of the detection apparatus, while the sixth end is configured in the third accommodating cavity.

According to exemplary embodiment of the invention, the material of the above chip body includes polymer.

According to the above exemplary embodiments, in the biochip of the invention, the probe of the detection apparatus is precluded from directly extending into the first accommodating cavity and the second accommodating cavity of the biochip. Hence, the fluid containing the to-be-detected cells is prevented from being directly contacted by the probe and contaminated.

The invention and certain merits provided by the invention can be better understood by way of the following exemplary embodiments and the accompanying drawings, which are not to be construed as limiting the scope of the invention.

DETAILED DESCRIPTION OF DISCLOSED EMBODIMENTS

Figure 1:
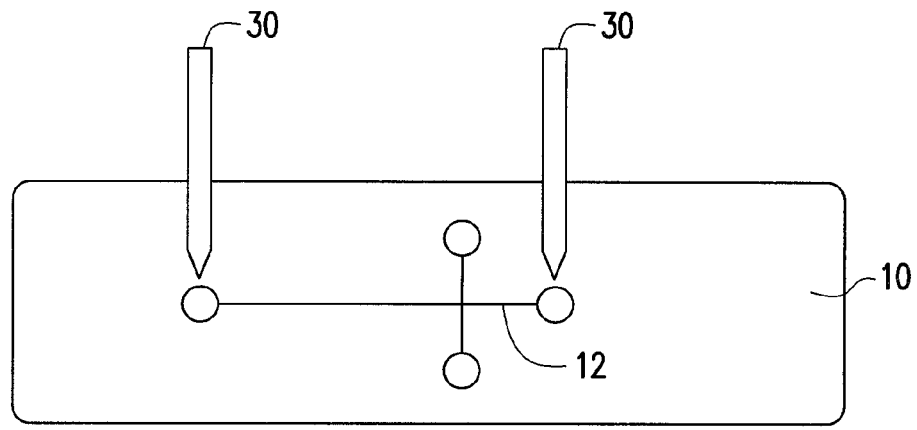
FIG. 1 is a schematic diagram of a conventional biochip.
Figure 2:
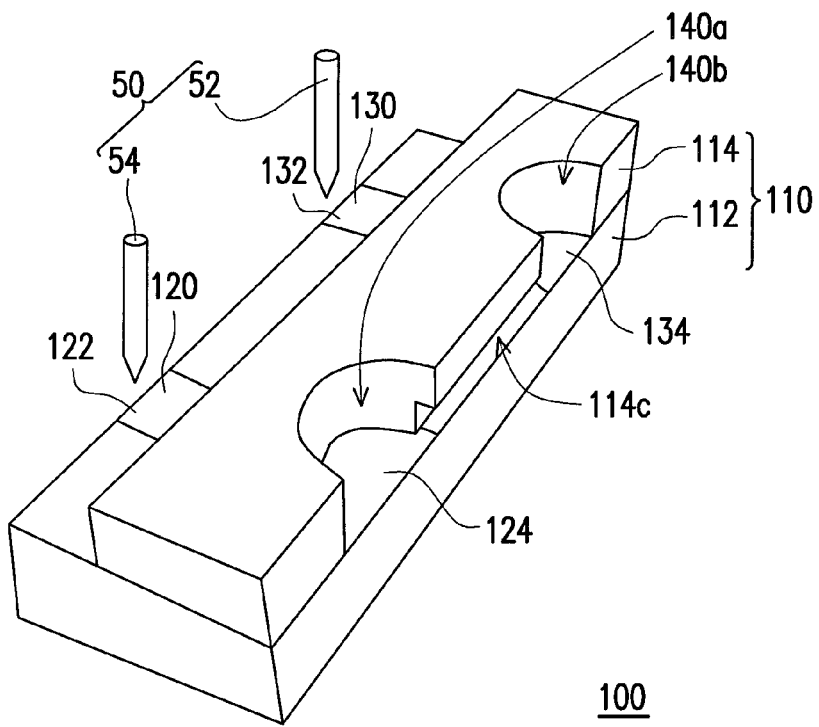
FIG. 2 is a schematic cross-section diagram of a biochip according to a first exemplary embodiment.
Figure 3:
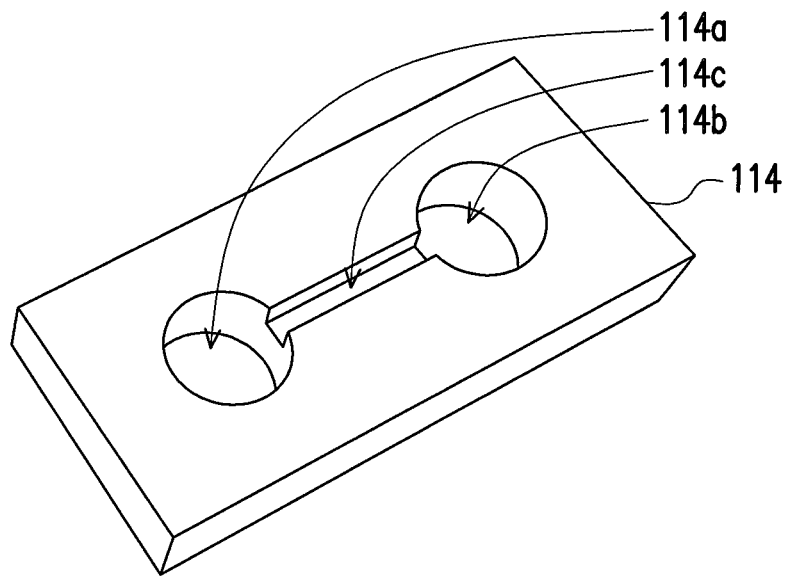
FIG. 3 is a schematic diagram of a second substrate of FIG. 2.

FIG. 2 is a schematic cross-section diagram of a biochip according to a first exemplary embodiment. FIG. 3 is a schematic diagram of a second substrate of FIG. 2. The second substrate in FIGS. 2 and 3 are shown upside down. Referring to both FIGS. 2 and 3, the biochip 100 in this exemplary embodiment includes a chip body 110, a first electrode 120, and a second electrode 130. The chip body 100 includes a first accommodating cavity 140a, a second accommodating cavity 140b, and a micro-fluid channel 114c. The micro-fluid channel 114c is connected with the first accommodating cavity 140a and the second accommodating cavity 140b. The first electrode 120 and the second electrode 130 are configured at the chip body 110. The first electrode 120 includes a first end 122 and a second end 124. The first end 122 serves to contact a first probe 52 of a first detection device 50, while the second end 124 is configured in the first accommodating cavity 140a. The second electrode 130 includes a third end 132 and a fourth end 134, and the third end 132 serves to contact the second probe 54 of the first detection device 50, while the fourth end is configured in the second accommodating cavity 140b.

According to the above configuration, the second end 124 of the first electrode 120 and the fourth end 134 of the second electrode 130 are respectively configured in the first accommodating cavity 140a and the second accommodating cavity 140b. The other ends of the first electrode 120 and the second electrode 130, which are respectively the first end 122 and the third end 132, are configured outside the first accommodating cavity 140a and the second accommodating cavity 140b. Hence, when a user uses the detection apparatus 50 to detect the biochip 100, the user only requires using the first probe 52 and the second probe 54 to respectively contact with and apply a bias to the first end 122 and the second end 132. The bias is then transmitted, through the second end 124 and the fourth end 134 to the fluid containing the to-be-detected cells in the first accommodating cavity 140a and the second accommodating cavity 140b to drive the fluid containing the to-be-detected cells to flow to perform the detection process. Alternatively speaking, the first probe 52 and the second probe 54 of the detection apparatus 50 will not be in direct contact with fluid containing the to-be-detected cells in the first accommodating cavity 140a and the second accommodating cavity 140b. Hence, after the detection process, it is not required to clean the first probe 52 and the second probe 54, and the next fluid sample containing the to-be-detected cells is precluded from being contaminated.

More specifically, the body 110 includes a first substrate 112 and a second substrate 114. The first electrode 120 and the second electrode 130 are disposed on the first substrate 112. The second substrate 114 includes the first through hole 114a, the second through hole 114b, and the fluid-micro channel 114c. The first through hole 114a forms the first accommodating cavity 140a, the second through hole 114b forms the second accommodating cavity 140b. The first through hole 114a and the second through hole 114b respectively expose the second end 124 and the fourth end 134. Hence, the second end 124 of the first electrode and the fourth end 134 of the second electrode 130 are respectively in contact with the fluid containing the to-be-detected cells in the first accommodating cavity 140a and the second accommodating cavity 140b. Moreover, the second substrate 114 is disposed on the first substrate 112, not covering the first end 122 and the third end 132 on the first substrate 112. Accordingly, the first end 122 and the third end 132 may contact with the first probe 52 and the second probe 54 of the detection apparatus 50. In this exemplary embodiment, the first probe 52 and the second probe 54 and the detection light beam approaches the biochip 100 from the top of FIG. 2. It is understood that the detection light beam may also approach the biochip 100 from the bottom of FIG. 2.

The following disclosure is in reference to a detection process of the biochip 100 of the invention. In an exemplary embodiment, the biochip detection apparatus 50 is a flow cytometer; however, it should be understood that the exemplary embodiment is presented by way of example and not by way of limitation. The fluid containing the to-be-detected cells is placed in the biochip 100. Then, a user uses the first probe 52 and the second probe 54 to respectively contact the first end 122 and the third end 132. Herein, a voltage, provided by the flow cytometer, drives the cells in the fluid, allowing the cells to flow in the micro-fluid channel.

Then, the flow cytometer inputs a detection light beam. Each cell suspended in the fluid passes through the detection light beam and a fluorescent light reaction is generated. These detection signals are recorded by a light detector (not shown) of the flow cytometer. According to the detection results, the number of cells is calculated and the physical property of the cells is outputted. Ultimately, the user removes the first probe 52 and the second probe 54 from the first end 122 and the third end 132 to complete the entire detection process. Since the first probe 52 and the second probe 54 are precluded from contacting with the fluid containing the to-be-detected cells, a cleaning procedure is not required after the detection process. Further, the fluid containing the to-be-detected cells to be detected in a next detection process is precluded from generating a chemical reaction and being contaminated.

Additionally, the first probe 52 and the second probe 54 may be designed to be flexible or compressible. In other words, when the first probe 52 and the second probe 54 respectively contact with the first end 122 and the second end 132, whether a contact has been achieved can be determined based on elastic recoil. A slightly higher force may be applied to ensure a good contact between the first probe 52 and the first end 122 and between the second probe 54 and the third end 132. In this exemplary embodiment, the first probe 52 and the second probe 54 maybe a pogo-pin. However, it should be understood that the above embodiments are presented by way of example and not by way of limitation.

Figure 4:
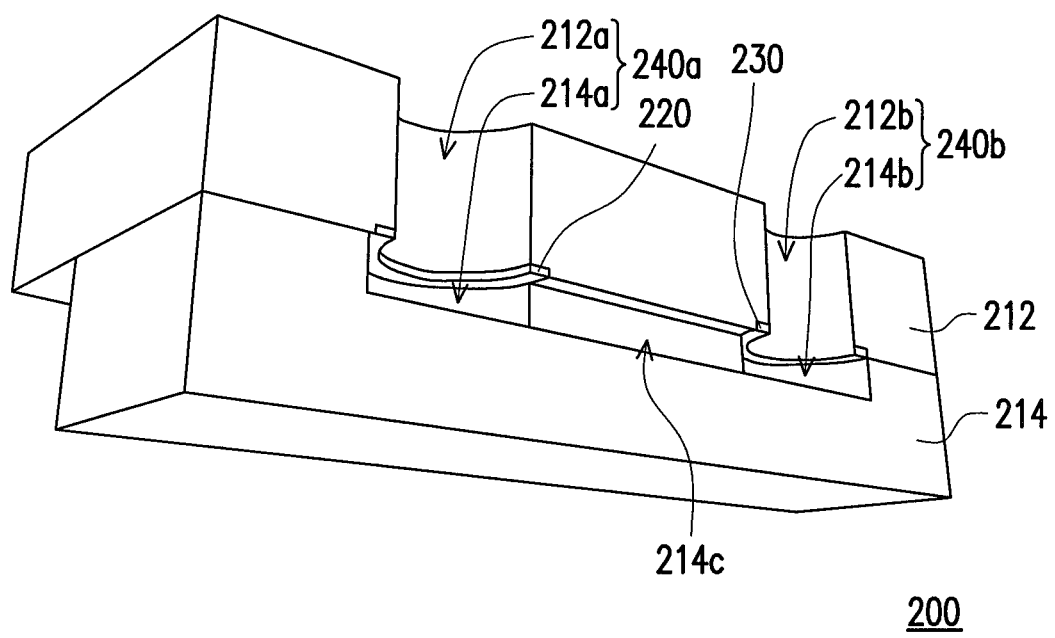
FIG. 4 is a schematic, cross-section diagram of a biochip according to a second exemplary embodiment of the invention.
Figure 5:
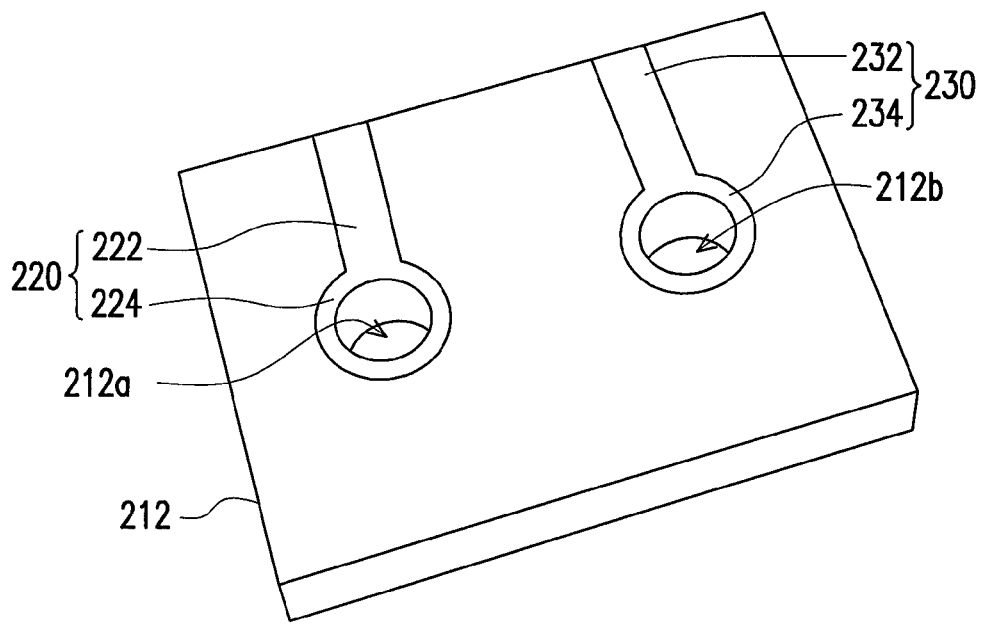
FIG. 5 is a schematic diagram of the first substrate in FIG. 4.

FIG. 4 is a schematic, cross-sectional view of a biochip according to a second exemplary embodiment of the invention. FIG. 5 is a schematic diagram of the first substrate in FIG. 4. The first substrate in FIGS. 4 and 5 are upside down. Referring to both FIGS. 4 and 5, the body 210 in this exemplary embodiment includes a first substrate 212 and a second substrate 214. The first substrate 212 includes a first through hole 212a and a second through hole 212b. The first electrode 220 and the second electrode 230 are disposed on the first substrate 212. The second end 224 encloses the first through hole 212a, the fourth end 234 encloses the second through hole 212b. The second substrate 214 includes first cavity 214a, a second cavity 214b and a micro-fluid channel 214c. The second end 224 and the fourth end 234 respectively expose the first cavity 214a and the second cavity 214b. The first through hole 212a and the first cavity 214a form a first accommodating cavity 240a. The second through hole 212b and the second cavity 214b form a second accommodating cavity 240b. The second substrate 214 is disposed under the first substrate 212, not covering the first end 222 and the third end 232. In this exemplary embodiment, the first probe and the second probe approaches the chip body 210 from the bottom of FIG. 4, while the detection light beam approaches the chip body 210 form the top of FIG. 4.

Figure 6:
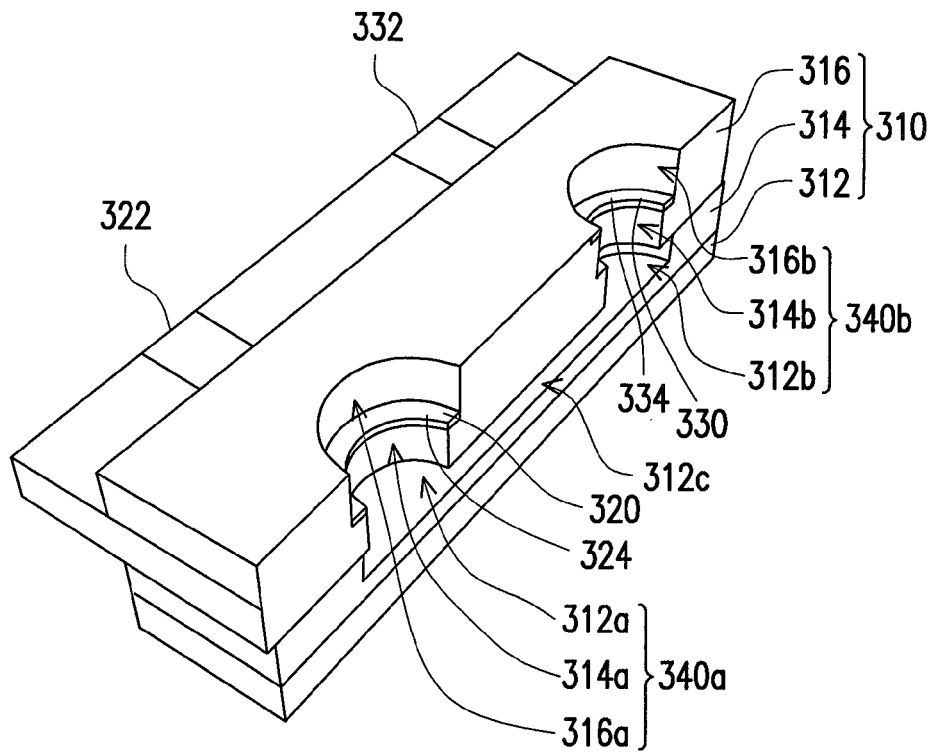
FIG. 6 is a schematic, cross-sectional diagram of a biochip according to a third exemplary embodiment of the invention.

FIG. 6 is a schematic, cross-sectional diagram of a biochip according to a third exemplary embodiment of the invention. Referring to FIG. 6, the chip body 310 includes a first substrate 312, a second substrate 314, and a third substrate 316. The first substrate 312 includes a first cavity 312a, a second cavity 312b, and a micro-fluid channel 312c. The second substrate 314 includes a first through hole 314a and a second through hole 314b. The second substrate 314 is disposed on the first substrate 312. The first electrode 320 and the second electrode 330 are disposed on the second substrate 314. The second end 324 encloses the first through hole 314a and the fourth end 334 encloses the second through hole 314b. The third substrate 316 includes a third through hole 316a and a fourth through hole 316b. The third substrate 316 is disposed on the second substrate 314, and the first end 322 and the third end 332 are not covered by the third substrate 316. The third through hole 316a and the fourth through hole 316b respectively expose the second end 324 and the fourth end 334. The first cavity 312a, the first through hole 314a, and the third through hole 316a form a first accommodating cavity 340a, while the second cavity 312b, the second through hole 324b, and a fourth through hole 316b form a second accommodating cavity 340b. In this exemplary embodiment, the first probe, the second probe, and the detection light beam approach the chip body 310 from the top of FIG. 6.

Figure 7:
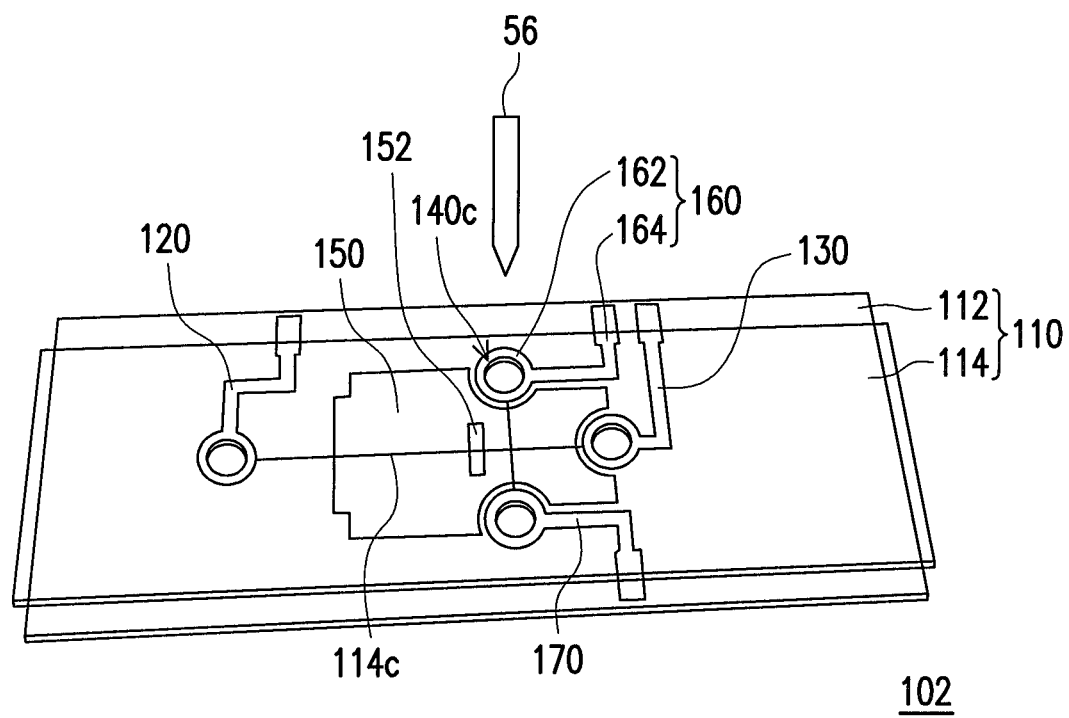
FIG. 7 is a schematic diagram of a biochip in FIG. 2.

FIG. 7 is a schematic diagram showing a slight modification of the biochip in FIG. 2. Wherever possible, the same reference numbers are used in the FIG. 7 and FIG. 2 to refer to the same or like parts. Referring the FIG. 7, the biochip 102 also includes a shield layer 150. The first electrode 120, the second electrode 130, and the shield layer 150 belong to a same patterned metal layer. In other words, the first electrode 120, the second electrode 130, and the shield layer 150 are formed from a same metal layer and are subjected to a single patterning process. The shield layer 150 is disposed on the chip body 110 and includes an optical window 152. The position of the optical window 152 corresponds to a section of the micro-fluid channel 114c. Hence, after the detection light beam provided by the flow cytometer 152 irradiates the shielding layer 150, the detection light beam is restricted to pass through at the optical window 152. Accordingly, no additional mechanism is required to be disposed on the flow cytometer to limit the region being irradiated by the light beam.

In this exemplary embodiment, the material of the chip body 110 may include polymer. Compare to the conventional glass body chip, polymer is easier to be possessed, and the time for fabricating a chip body is reduced. Moreover, a material of the chip body 110 may include a hard polymer material, such as polymetholmethacrylate (PMMA), polycarbonate (PC), etc. According to the conventional application of poly(dimethlysiloxane) (PDMS) in forming a chip body, the chip body must be subjected to a plasma treatment prior to any detection process is performed because PDMS is a hydrophobic silicon. In contrast, the PMMA, as applied in the invention, is precluded from the plasma treatment. Accordingly, a prolong detection time is obviated.

In addition, the biochip 110 of an exemplary embodiment of the invention further includes a third electrode. The third electrode 160 is disposed at the chip body 110 and includes a fifth end 162 and a sixth end 164. The chip body 110 further includes a third accommodating cavity 140c connected to a micro-fluid channel 114c. The fifth end 162 serves to contact a third probe 56 of the detection device 50, and a sixth end 166 is configured in the third accommodating cavity 140c. Accordingly, the fluid containing the to-be-detected cells in the micro-fluid channel 114c in FIG. 6 flows in a direction from first electrode 160 to second electrode 130, from the first electrode 120 to the third electrode 160, or from the second electrode 130 to the third electrode 160. Hence, a user may select an appropriate electrode to apply a bias to for controlling the flow direction. In other words, the user may choose to apply a bias between the first electrode 120, the second electrode 130, and the third electrode 160 to improve the flow agility of the fluid containing the to-be-detected cells in the micro-fluid channel 114c. Further, the numbers of the electrode and the accommodating cavity are not limited. For example, the biochip 102 may expand to include a fourth electrode 170.

According to the above disclosure, in the biochip of the exemplary embodiments of the invention one end of the electrode serves to contact the probe of the detection apparatus, while another end of the electrode serves to connect with the accommodating cavity. Accordingly, when a bias is applied to the probe of the detection apparatus, it is not necessary for the probe to contact with the fluid containing the to-be-detected cells in the accommodating cavity. Hence, the probe is precluded from being contaminated by the fluid containing the to-be-detected cells. Moreover, the biochip is fabricated with a polymer material; hence, the chip is easier to be processed to reduce the fabrication time thereof. Moreover, based on the detection requirement, the number of electrodes on the chip may be increased, and the user may select an appropriate electrode for applying a bias to control the flow direction of the fluid.

In addition, through disposing an optical window on a biochip, designing a mechanism on the detection apparatus to limit the detection light beam is precluded, which is beneficial in preventing noise.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A biochip, comprising:
   a chip body, comprising a first accommodating cavity, a second accommodating cavity, and a micro-fluid channel, wherein the micro-fluid channel is connected with the first accommodating cavity and the second accommodating cavity;
   a first electrode disposed at the chip body and comprising a first end and a second end, wherein the first end serves to contact a first probe of a detection apparatus, the second end is configured in the first accommodating cavity, the first end is configured outside of the first accommodating cavity, and the first electrode extends from the second end in the first accommodating cavity to the first end outside of the first accommodating cavity; and
   a second electrode, configured at the chip body and comprising a third end and a fourth end, wherein the third end serves to contact a second probe of the detection apparatus, the fourth end is configured in the second accommodating cavity, the third end is configured outside of the second accommodating cavity, and the second electrode extends from the fourth end in the second accommodating cavity to the third end outside of the second accommodating cavity.

2. The biochip of claim 1, wherein the chip body comprises:
   a first substrate, wherein the first electrode and the second electrode are disposed on the first substrate; and
   a second substrate, comprising a first through hole, a second through hole, and the micro-fluid channel, wherein the second substrate is disposed on the first substrate, not covering the first end and the third end, and the first through hole and the second through hole respectively expose the second end and the fourth end, and the first through hole forms the first accommodating cavity, and the second through hole forms the second accommodating cavity.

3. The biochip of claim 1, wherein the chip body comprises:
   a first substrate, comprising a first through hole and a second through hole, wherein the first electrode and the second electrode are disposed on the first substrate, and the second end encloses the first through hole, and the fourth end encloses the second through hole; and
   a second substrate, comprising a first cavity, a second cavity, and the micro-fluid channel, wherein the second substrate is disposed on the first substrate, not covering the first end and the third end, and the second end and the fourth end are respectively exposed at the first cavity and the second cavity, and the first through hole and the first cavity forms the first accommodating cavity, and the second through hole and the second cavity form the second accommodating cavity.

4. The biochip of claim 1, wherein the chip body comprises:
   a first substrate, comprising a first cavity, a second cavity, and the micro-fluid channel;
   a second substrate, comprising a first through hole and a second through hole, wherein the second substrate is disposed on the first substrate, and the first electrode and the second electrode are disposed on the second substrate, and the second end encloses the first through hole, and the four end encloses the second through hole; and
   a third substrate, comprising a third through hole and a fourth through hole, wherein the third substrate is disposed on the second substrate, not covering the first end and the third end, and the third through hole and the fourth through hole respectively expose the second end and the fourth end, and the first cavity, the first through hole, and the third through hole form the first accommodating cavity, while the second cavity, the second through hole, and the fourth through hole form the second accommodating cavity.

5. The biochip of claim 1 further comprising a third electrode disposed at the chip body, and the third electrode comprising a fifth end and a sixth end, wherein the chip body further comprises a third accommodating cavity connected to the micro-fluid channel, and the fifth end serves to contact with a third probe of the detection apparatus, and the sixth end is configured in the third accommodating cavity.

6. The biochip of claim 1, wherein a material of the biochip comprises polymer.

7. The biochip of claim 1 further comprising a shielding layer, disposed at the chip body, the shielding layer comprising an optical window corresponding to a section of the micro-fluid channel.

8. The biochip of claim 7, wherein the first electrode, the second electrode, and the shielding layer belong to a same patterned metal layer.

* * * * *